United States Patent [19]
Dreikorn et al.

[11] Patent Number: 5,326,766
[45] Date of Patent: Jul. 5, 1994

[54] 4-(2-(4-(2-PYRIDINYLOXY)PHENYL)E-THOXY)QUINAZOLINE AND ANALOGUES THEREOF

[76] Inventors: Barry A. Dreikorn, 5 All Saints Close, Marcham, Oxfordshire, England, OX 136 PE; Sylvester V. Kaster, 8720 Rosewood La., Indianapolis, Ind. 46240; Neil V. Kirby, 9731 Trilobi Dr., Indianapolis, Ind. 46236; Robert G. Suhr, 1522 Bruner Dr., Greenfield, Ind. 46140; Brian R. Thoreen, 7344 Crickwood Pl., Indianapolis, Ind. 46268

[21] Appl. No.: 932,431

[22] Filed: Aug. 19, 1992

[51] Int. Cl.[5] .................. C07D 247/02; C07D 401/12; C07D 401/10; A61K 31/505
[52] U.S. Cl. ..................................... 514/259; 544/238; 544/257; 544/258; 544/284; 544/333; 544/279; 544/405; 546/133; 546/137; 546/152; 546/155; 546/157; 546/159; 546/176; 546/177
[58] Field of Search .................. 544/284; 514/259

[56] References Cited
U.S. PATENT DOCUMENTS

| | | | |
|---|---|---|---|
| 4,668,966 | 5/1987 | Zink | 544/284 |
| 5,162,325 | 11/1992 | Chakravarty | 544/284 |

FOREIGN PATENT DOCUMENTS

| | | |
|---|---|---|
| 326331 | 8/1989 | European Pat. Off. |
| 414386 | 2/1991 | European Pat. Off. |

*Primary Examiner*—Mark L. Berch

[57] ABSTRACT

Compounds of the formula (I):

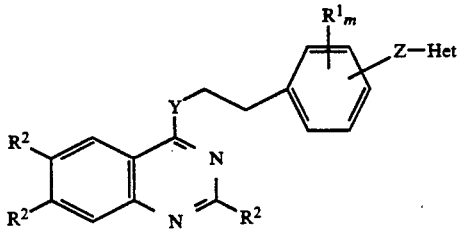

wherein:

Het is pyridyl, pyrazinyl, pyrimidinyl, or pyridizinyl, optionally substituted with one or more groups selected from halo, lower alkyl, lower alkoxy, haloalkyl, haloalkoxy, $NO_2$, CN, and lower alkoxy-carbonyl;

Z is a C—C single bond, $CH_2$, NH, O, S, —$CH_2O$—, or —$OCH_2$—; and the remaining groups are as defined in the specification are useful as pesticides.

19 Claims, No Drawings

4-(2-(4-(2-PYRIDINYLOXY)PHENYL)ETHOXY)-QUINAZOLINE AND ANALOGUES THEREOF

FIELD OF THE INVENTION

This invention provides new organic compounds having exceptional fungicidal, insecticidal, miticidal, and nematicidal activity. The invention also provides new pesticide methods and compositions utilizing the new compounds.

More specifically, the invention provides new compounds of the formula (I):

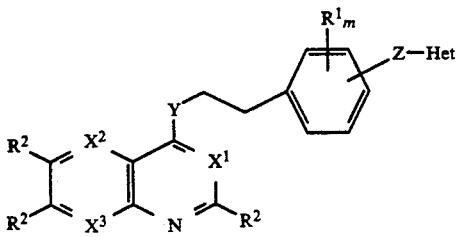

wherein:

Het is pyridyl, pyrazinyl, pyrimidinyl, or pyridizinyl, optionally substituted with one or more groups selected from halo, lower alkyl, lower alkoxy, haloalkyl, haloalkoxy, $NO_2$, CN, and lower alkoxy-carbonyl;

Z is a C—C single bond, $CH_2$, NH, O, S, $—CH_2O—$, or $—OCH_2—$;

m is 4;

$R^1$ are independently H, halo, lower alkyl, lower alkoxy, haloalkyl, haloalkoxy, $NO_2$, CN, lower alkoxy-carbonyl, O-phenyl, or O-substituted phenyl;

Y is $CH_2$, $NR^3$, or O, where $R^3$ is selected from H, lower alkyl, lower alkyl-carbonyl, lower alkyl-carbonyloxy, $SO_q$-lower alkyl, $SO_q$-phenyl or substituted phenyl; and q is an integer from 0 to 2;

$X^1$, $X^2$, and $X^3$ are independently N or $CR^2$;

$R^2$ are independently H, halo, lower alkyl, lower alkoxy, haloalkyl, haloalkoxy, $NO_2$, CN, or lower alkoxy-carbonyl;

or an N-oxide or salt thereof.

The invention also provides new pesticide methods and compositions utilizing the compounds of formula (I).

DETAILED DESCRIPTION OF THE INVENTION

The invention is directed to compounds of formula (I) wherein Het is an optionally substituted six-membered heterocyclic system containing one or two nitrogen atoms. More specifically, Het is selected from:

optionally substituted pyridyl

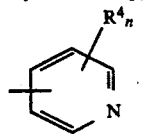

optionally substituted pyrazinyl

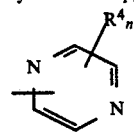

optionally substituted pyrimidinyl

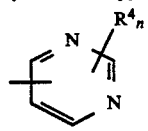

optionally substituted pyridazinyl

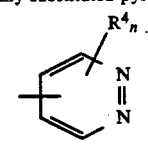

where n is 4 in the case of pyridyl and 3 in the case of pyrazinyl, pyrimidinyl, and pyridazinyl, and $R^4$ are independently H, halo, lower alkyl, lower alkoxy, haloalkyl, haloalkoxy, $NO_2$, CN, and lower alkoxy-carbonyl.

Throughout this document, all temperatures are given in degrees Celsius, and all percentages are weight percentages unless otherwise stated.

The term "halo" refers to F, Cl, Br, and I atoms.

The term "lower alkyl" refers to C1 to C6 straight hydrocarbon chains and C3 to C6 branched and cyclic hydrocarbon groups.

The terms "lower alkenyl" and "lower alkynyl" refer to C2 to C6 straight hydrocarbon chains and C3 to C6 branched hydrocarbon groups containing at least one unsaturated bond.

The terms "lower alkoxy" and "lower alkylthio" refer to O-lower alkyl and S-lower alkyl groups.

The term "haloalkyl" refers to lower alkyl groups substituted with one or more halo atoms.

The term "haloalkoxy" refers to lower alkoxy groups substituted with one or more halo atoms.

The term "substituted phenyl" refers to phenyl substituted with lower alkyl, lower alkenyl, lower alkynyl, lower alkoxy, lower alkylthio, halo, hydroxy, $NO_2$, haloalkyl, haloalkoxy, haloalkylthio, CN, phenyl, substituted phenyl, O-phenyl, O-substituted phenyl, $C_1$-$C_4$ alkanoyloxy, benzyloxy, or $S(O)_pAlk$, where p is 1-2.

The term "HPLC" refers to a high pressure liquid chromatography.

In the present invention, whenever multiple substituents are independently selected it is to be understood that they are selected so as to be sterically compatible with each other. Steric compatibility refers to the absence of steric hindrance as this term is defined in The Condensed Chemical Dictionary, 7th edition, Reinhold Publishing Co., N.Y. page 893 (1966), which definition is as follows:

steric hindrance. A characteristic of molecular structure in which the molecules have a spatial arrangement of their atoms such that a given reaction with another molecule is prevented or retarded in rate.

Steric compatibility is characterized by substituents whose physical bulk does not require confinement within volumes insufficient for the exercise of their normal behavior as discussed in D. J. Cram and G. Hammon, Organic Chemistry 2nd edition, McGraw-Hill Book Company, N.Y. page 215 (1964).

PREFERRED EMBODIMENTS

While all of the compounds of formula (I) exhibit exceptional activity as plant fungicides and insecticides, certain categories of compounds are preferred, namely:

1. compounds of formula (I) wherein Het is pyridyl optionally substituted with one or more groups selected from halo, lower alkyl, lower alkoxy, haloalkyl, haloalkoxy, $NO_2$, CN, and lower alkoxy-carbonyl, i.e. compounds wherein Het is

[structure: pyridyl with $R^4_n$]

where n is 4, and $R^4$ are independently H, halo, lower alkyl, lower alkoxy, haloalkyl, haloalkoxy, $NO_2$, CN, and lower alkoxy-carbonyl;

2. compounds of formula (I) wherein Het is 2-pyridyl optionally substituted with one or more groups selected from halo, lower alkyl, lower alkoxy, haloalkyl, haloalkoxy, $NO_2$, CN, and lower alkoxy-carbonyl, i.e. compounds wherein Het is

[structure: 2-pyridyl with $R^4_n$]

where n is 4, and $R^4$ are independently H, halo, lower alkyl, lower alkoxy, haloalkyl, haloalkoxy, $NO_2$, CN, and lower alkoxy-carbonyl;

3. compounds of formula (IA):

[structure of formula (IA)]

where n is 4; $R^4$ are independently H, halo, lower alkyl, lower alkoxy, haloalkyl, haloalkoxy, $NO_2$, CN, and lower alkoxy-carbonyl; and Z, Y, $X^1$, $X^2$, $X^3$ and $R^2$ are as defined for formula (I);

4. compounds of formula (I) wherein $X^1$ is N and $X^2$ and $X^3$ are $CR^2$;

5. compounds of formula (IB):

[structure of formula (IB)]

where n is 4; $R^4$ are independently H, halo, lower alkyl, lower alkoxy, haloalkyl, haloalkoxy, $NO_2$, CN, and lower alkoxy-carbonyl; and Z, Y, and $R^2$ are as defined for formula (I);

6. compounds of formula (IB) wherein $R^2$ is an 8-fluoro group;

7. compounds of formula (IB) wherein $R^2$ is H;

8. compounds of formula (I), (IA), and (IB) wherein Y is O;

9. compounds of formula (I), (IA), and (IB) wherein Z is O;

10. compounds of formula (I), (IA), and (IB) wherein Y and Z are both O;

11. compounds of formula (IA) and (IB) wherein n is 1 or 2 and $R^4$ is halo, lower alkyl, alkoxy, haloalkoxy, haloalkyl, cyano, or nitro;

12. compounds of formula (I) or (IA) wherein n is 1, 2, or 3, and $R^4$ are halo.

13. compounds of formula (I) or (IA) wherein at least two of $R^1$ are selected from H and F and at least three of $R^2$ are selected from H and F.

SYNTHESIS

The compounds of this invention are made using well known chemical procedures. The required starting materials are commercially available or are readily synthesized using standard procedures.

Synthesis of Compounds wherein Y is O

The compounds of formula (I) wherein Y is O can be made by condensing a compound of formula (II)

[structure of formula (II)]

where $X^1$, $X^2$, $X^3$ and $R^2$ are as defined for formula (I); and L is a leaving group, such as F, Cl, Br, I, $NO_2$, 1,2,3-triazol-1-yl, 1,2,4-triazol-1-yl, $OSiMe_3$, arylthio, alkylthio, alkylsulfonyl, arylsulfonyl, alkoxy, or arylsulfinyl; with an alcohol of the formula

[structure with HO-, $R^1_m$, Z—Het]

where Het, Z, $R^1$ and m are as defined for formula (I). The reaction is preferably carried out in the presence of a strong base, such as sodium hydride, in a non-reactive solvent, such as DMF, at a temperature in the range of 0° to 25° C.

Synthesis of Compounds wherein Y is NH or N-lower alkyl

The compounds of formula (I) wherein Y is NH or N-lower alkyl are prepared by condensing a compound of formula (II), as defined above, with an amine of the formula

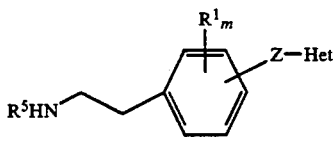

where Het, Z, $R^1$ and m are as defined for formula (I); and $R^5$ is H or lower alkyl. The compound of formula (II) is allowed to react with the amine at a temperature in the range 20°–180° C., preferably in the presence of an acid acceptor, such a triethylamine. The reaction may be carried out neat, or in a nonreactive organic solvent.

Compounds of formula (I) where $R^3$ is acyl are prepared from amines where $R^3$ is H by reacting them with an acylating agent such as acetyl chloride or acetic anhydride.

Synthesis of Compounds wherein Y is $CH_2$

Compounds of formula (I) wherein Y is $CH_2$ are prepared by reacting a compound of formula (III)

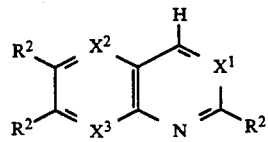

where $X^1$, $X^2$, $X^3$ and $R^2$ are as defined for formula (I); with a Grignard reagent of the formula

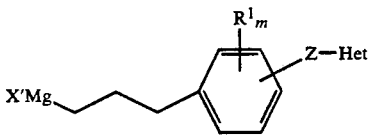

where Het, Z, $R^1$ and m are as defined for formula (I) and X' is halo; to provide a 3,4-dihydro quinazoline or quinoline, which is then oxidized.

Compounds of formula (I) wherein Y is $CH_2$ may also be prepared by reacting a compound of formula (III) with a lithio reagent of the formula

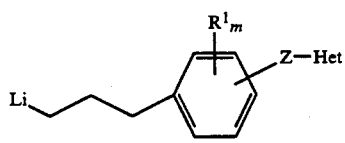

where Het, Z, $R^1$ and m are as defined for formula (I) to provide a 3,4-dihydro quinazoline or quinoline, which is then oxidized. The desired compound of the invention may then be separated from other products using conventional means. Typical reaction conditions are those described in Armarego and Smith, *J. Chem Soc.*, page 5360 (1965).

The compounds of formula (I) wherein Y is $CH_2$ can also be made by reacting a compound (IV)

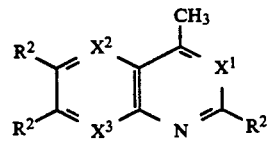

where $X^1$, $X^2$, $X^3$ and $R^2$ are as defined for formula (I); with an aprotic organolithium base, especially lithium diisopropylamide, in a polar aprotic solvent and then reacting with a compound of the formula (V)

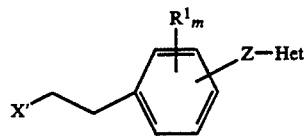

where Het, Z, $R^1$, and m are as defined above, and X' is halo.

Such reactions are preferably carried out at low temperatures, preferably $-78°$ to $0°$ C.

The compounds of formula (I) wherein Y is $CH_2$ can also be made by the process described in the *J. Heterocyclic Chemistry, Vol.* 14. 1081–1083 (1977) by A. Scoville and F. X. Smith. This procedure involves hydrolysis and decarboxylation of substituted barbituric acids of the formula (VI)

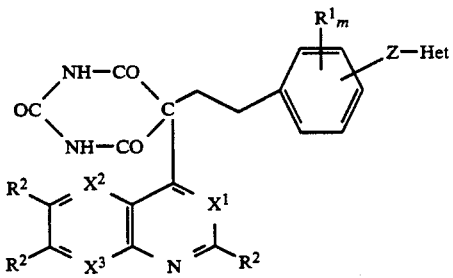

wherein the variable substituents are as defined for formula (I). The barbituric acid derivative is dissolved in a solution of sodium hydroxide and water and refluxed. The solution is then made slightly acidic and again refluxed.

PREPARATION 1

2-(4-(5-(Trifluoromethyl)-2-pyridinyloxy)phenyl)ethanol

The sodium salt of p-hydroxyphenyl acetic acid ethyl ester was prepared using sodium hydride in DMF. To a DMF solution containing approximately 0.1 mol of this salt was added 0.1 mol of 2-chloro-5-(trifluoromethyl)-pyridine at $-5°$ C. The mixture warmed slowly to reflux. It was then poured into an ice/water mixture, extracted with ether, dried, producing 27 g of crude (4-(5-(trifluoromethyl)-2-pyridinyloxy)phenyl)acetic acid ethyl ester as an oil. The crude product was purified on a column with 20% ethyl acetate/pentane, to give 17 g of the ester as an oil.

The (4-(5-(trifluoromethyl)-2-pyridinyloxy)phenyl)acetic acid ethyl ester (15.6 g, 48 mmol) was then added to a slurry of lithium aluminum hydride (2.3 g, 60 mmol) in ethyl ether (500 mL). The mixture was stirred overnight at room temperature. Then a saturated solution of ammonium chloride in water was added, and the title product, an oil, was separated from remaining solids by filtration. Yield 11 g.

EXAMPLE 1

8-Fluoro-4-(2-(4-(5-(trifluoromethyl)-2-pyridinyloxy)-phenyl)ethoxy)quinazoline (Compound 27)

A mixture of 4-chloro-8-fluoroquinazoline (2.12 g, 12 mmol) and 2-(4-(5-(trifluoromethyl)-2-pyridinyloxy)-phenyl)ethanol (2.83 g, 10 mmol) in 50 mL of toluene containing a catalytic amount of hydrogen chloride was stirred for several days. The title product was isolated by column chromatography. Yield 1.6 g. MP 116°–118° C.

PREPARATION 2

2-(4-(5-Trifluoromethyl-2-pyridinyloxy)phenyl)ethylamine

Sodium hydride (0.78 g, 0.033 mol) was slurried in dry DMF (50 mL) and tyramine (4.31 g, 0.031 mol) added. The mixture was stirred at room temperature until effervescence ceased. A solution of 2-chloro-5-trifluoromethylpyridine (6.0 g, 0.033 mol) in DMF (10 mL) was then added. The mixture was heated at 50° C. for three hours and poured into water. This was extracted with ethyl acetate and the organic phase washed with water and dried over anhydrous sodium sulphate. Evaporation of the solvent under reduced pressure and purification of the product by column chromatography gave 7.5 g of product as an oil.

EXAMPLE 2

8-Fluoro-4-(2-(4-(5-(trifluoromethyl)-2-pyridinyloxy)-phenyl)ethylamino)quinazoline (Compound 28)

A mixture of 4-chloro-8-fluoroquinazoline (1.82 g, 0.01 mol), 2-(4-(5-trifluoromethyl-2-pyridinyloxy)-phenyl)ethylamine (2.82 g, 0.01 mol), triethylamine (1.1 g, 0.011 mol) and ethanol (50 mL) was heated under reflux for three hours and allowed to cool. Solvent was evaporated under reduced pressure, and the residue dissolved in dichloromethane. This was washed with 0.5M sodium hydroxide solution and water, and dried over anhydrous sodium sulphate. Evaporation of the solvent under reduced pressure and recrystallization from ethyl acetate:hexane gave 2.5 g of product. MP 152° C.

EXAMPLE 3

4-(2-(4-(5-Trifluoromethyl)-2-pyridinyloxy)phenyl)ethylamino)pyrido[3,2-d]pyrimidine (Compound 32)

A mixture of 2-(4-(5-trifluoromethyl-2-pyridinyloxy)-phenyl)ethylamine (2.0 g, 7.1 mmol), 4-[1'-(1,2,4-triazolo)pyrido[3,2-d]pyrimidine (1.4 g, 7.1 mmol), triethylamine (0.8 g, 8 mmol) and toluene (30 mL) was heated under reflux overnight and cooled. Solvent was evaporated under reduced pressure, and the residue was dissolved in dichloromethane. This was washed with 0.5M sodium hydroxide solution and water, and dried over anhydrous sodium sulphate. Evaporation of the solvent under reduced pressure and recrystallization from ethyl acetate:hexane gave 1.8 g of product. MP 102° C.

EXAMPLE 4

4-(2-(4-(5-Trifluoromethyl)-2-pyridinyloxy)phenyl)ethylamino)pyrido[2,3-d]-pyrimidine (Compound 31)

A mixture of 2-(4-(5-trifluoromethyl-2-pyridinyloxy)-phenyl)ethylamine (2.0 g, 7.1 mmol), 4-[1'-(1,2,4-triazolo)pyrido[2,3-d]pyrimidine (1.4 g, 7.1 mmol), triethylamine (0.8 g, 8 mmol) and toluene (30 mL) was heated under reflux overnight and then cooled. Solvent was evaporated under reduced pressure, and the residue was dissolved in dichloromethane. This was washed with 0.5M sodium hydroxide solution and water, and dried over anhydrous sodium sulphate. Evaporation of the solvent under reduced pressure and recrystallization from ethyl acetate gave 1.3 g of product. MP 185° C.

EXAMPLE 5

8-Fluoro-4-(2-(4-(6-(trifluoromethyl)-2-pyridinyloxy)-phenyl)ethylamino)quinoline (Compound 40)

A mixture of 4-chloro-8-fluoroquinoline (1.81 g, 0.01 mol), and 2-(4-(6-trifluoromethyl-2-pyridinyloxy)-phenyl)ethylamine (2.82 g, 0.01 mol), triethylamine (1.1 g, 0.011 mol) was heated at 180°–190° C. for two hours and allowed to cool to a glass. Dichloromethane (50 mL) and concentrated ammonia solution (50 mL) were added, and the mixture was stirred until the glass dissolved. The organic phase was washed with 0.5M sodium hydroxide solution and water, and was dried over anhydrous sodium sulphate. Evaporation of the solvent under reduced pressure and recrystallization from ethyl acetate:hexane gave 2.5 g of product. MP 157° C.

The following Table I identifies representative compounds of formula (I), together with characterizing physical data.

TABLE I

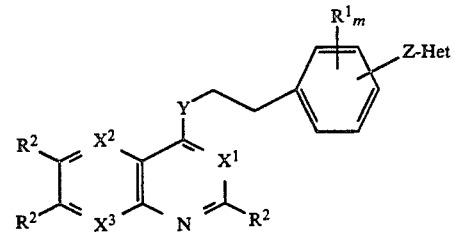

COMPOUND IDENTIFICATION

| Compound | $X^1$ | $X^2$ | $X^3$ | $R^2$ | $R^1_m$ | Y | Z | Het | MP °C. |
|---|---|---|---|---|---|---|---|---|---|
| 1 | N | CH | CH | 8-F | $H_4$ | NH | O | 3-chloro-5-trifluoromethyl-2-pyridyl | 170 |
| 2 | CH | N | CH | CH | $H_4$ | NH | O | 3-chloro-5-trifluoromethyl-2-pyridyl | 107 |

TABLE I-continued

COMPOUND IDENTIFICATION

| Compound | X¹ | X² | X³ | R² | R¹$_m$ | Y | Z | Het | MP °C. |
|---|---|---|---|---|---|---|---|---|---|
| 3 | N | CH | CH | 8-F | H₄ | O | O | 3-cyano-2-pyridyl | 165 |
| 4 | N | CH | CH | 5-F | H₄ | O | O | 3-cyano-2-pyridyl | 158 |
| 5 | N | CH | CH | 8-F | H₄ | O | O | 3-fluoro-5-trifluoromethyl-2-pyridyl | 84 |
| 6 | N | CH | CH | 8-F | H₄ | NH | O | 3-fluoro-5-trifluoromethyl-2-pyridyl | 167 |
| 7 | N | CH | CH | 5-F | H₄ | O | O | 3-fluoro-5-trifluoromethyl-2-pyridyl | 110 |
| 8 | N | CH | CH | 8-F | H₄ | O | O | 3-nitro-2-pyridyl | 142 |
| 9 | N | CH | CH | 5-F | H₄ | O | O | 3-nitro-2-pyridyl | 115 |
| 10 | N | CH | CH | 8-F | H₄ | O | O | 3-trifluoromethyl-2-pyridyl | 86 |
| 11 | N | CH | CH | 8-F | H₄ | NH | O | 3-trifluoromethyl-2-pyridyl | 171 |
| 12 | N | CH | CH | 8-F | H₄ | O | O | 4-trifluoromethyl-2-pyridyl | 130 |
| 13 | N | CH | CH | H | H₄ | O | O | 4-trifluoromethyl-2-pyridyl | 121 |
| 14 | N | CH | CH | 8-F | H₄ | NH | O | 4-trifluoromethyl-2-pyridyl | 171 |
| 15 | N | CH | CH | 8-F | H₄ | NH | O | 5-(methane-sulphonyl)-2-pyridyl | 211 |
| 16 | N | CH | CH | 5-F | H₄ | O | O | 5-chloro-2-pyridyl | 153 |
| 17 | N | CH | CH | 8-F | H₄ | O | O | 5-chloro-2-pyridyl | 116 |
| 18 | N | CH | CH | H | H₄ | O | O | 5-chloro-3-trifluoromethyl-2-pyridyl | 107 |
| 19 | N | CH | CH | 8-F | H₄ | O | O | 5-chloro-3-trifluoromethyl-2-pyridyl | 73 |
| 20 | N | CH | CH | 8-F | H₄ | O | O | 5-cyano-2-pyridyl | 195 |
| 21 | N | CH | CH | H | H₄ | O | O | 5-cyano-2-pyridyl | 155 |
| 22 | N | CH | CH | 8-F | H₄ | NH | O | 5-cyano-2-pyridyl | 156 |
| 23 | N | CH | CH | 8-F | H₄ | O | O | 5-nitro-2-pyridyl | 156 |
| 24 | N | CH | CH | 8-F | H₄ | NH | O | 5-nitro-2-pyridyl | 195 |
| 25 | N | CH | CH | 8-F | H₄ | O | O | 5-trichloromethyl-2-pyridyl | 108 |
| 26 | N | CH | CH | H | H₄ | O | O | 5-trichloromethyl-2-pyridyl | 40 |
| 27 | N | CH | CH | 8-F | H₄ | O | O | 5-trifluoromethyl-2-pyridyl | 117 |
| 28 | N | CH | CH | 8-F | H₄ | NH | O | 5-trifluoromethyl-2-pyridyl | 152 |
| 29 | N | CH | CH | H | H₄ | NH | O | 5-trifluoromethyl-2-pyridyl | 159 |
| 30 | CH | CH | N | CH | H₄ | O | O | 5-trifluoromethyl-2-pyridyl | a736–177 |
| 31 | CH | CH | N | CH | H₄ | NH | O | 5-trifluoromethyl-2-pyridyl | 185 |
| 32 | CH | N | CH | CH | H₄ | NH | O | 5-trifluoromethyl-2-pyridyl | 102 |
| 33 | N | CH | CH | 8-F | H₄ | O | O | 6-(2,2,2-trifluoroethoxy)-2-pyridyl | 97 |
| 34 | N | CH | CH | 8-F | H₄ | O | O | 6-chloro-4-trichloromethyl)-2-pyridyl | >40 |
| 35 | N | CH | CH | 8-F | H₄ | NH | O | 6-methoxy-4-trichloromethyl)-2-pyridyl | 174 |
| 36 | N | CH | CH | 8-F | H₄ | O | O | 6-trifluoromethyl-2-pyridyl | 114 |
| 37 | N | CH | CH | 8-F | H₄ | NH | O | 6-trifluoromethyl-2-pyridyl | 167 |
| 38 | N | CH | CH | H | H₄ | NH | O | 6-trifluoromethyl-2-pyridyl | 134 |
| 39 | N | CH | CH | 6-CH₃ | H₄ | NH | O | 6-trifluoromethyl-2-pyridyl | 133 |
| 40 | CH | CH | CH | 8-F | H₄ | NH | O | 6-trifluoromethyl-2-pyridyl | 157 |
| 41 | N | CH | CH | 8-F | H₄ | O | O | 3,5-dichloro-2-pyridyl | 126 |
| 42 | N | CH | CH | 8-F | H₄ | O | O | 3,5,6-trichloro-2- | 147 |

TABLE I-continued

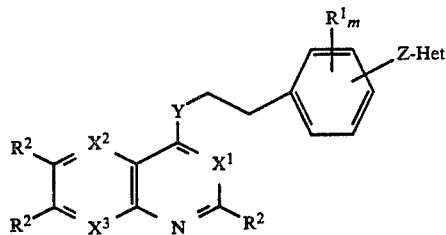

COMPOUND IDENTIFICATION

| Compound | X¹ | X² | X³ | R² | R¹$_m$ | Y | Z | Het | MP °C. |
|---|---|---|---|---|---|---|---|---|---|
| 43 | N | CH | CH | 5-F | H₄ | O | O | 3,5,6-trichloro-2-pyridyl | 162 |
| 44 | N | CH | CH | 8-F | H₄ | O | O | 3,5,6-trichloro-2-pyridyl | 131 |
| 45 | N | CH | CH | H | H₄ | O | O | 2-pyrimidinyl | 136 |
| 46 | N | CH | CH | H | H₄ | O | O | 5-bromo-2-pyrimidinyl | 140 |
| 47 | N | CH | CH | H | H₄ | O | O | 5-chloro-2-pyrimidinyl | 154 |
| 48 | CH | CH | CH | 8-F | H₄ | O | O | 5-chloro-2-pyrimidinyl | oil |
| 49 | N | CH | CH | H | H₄ | O | O | 6-chloro-3-pyridazinyl | 131 |
| 50 | N | CH | CH | H | H₄ | O | O | 6-chloro-5-(2-chloro-1,1-diemthyl-ethyl)-3-pyridazinyl | oil |
| 51 | N | CH | CH | H | H₄ | O | O | 2-pyrazinyl | |
| 52 | N | CH | CH | H | H₄ | O | O | 5-cyano-2-pyrimidinyl | |
| 53 | N | CH | CH | H | H₄ | O | O | 2-chloro-4-pyrimidinyl | 140 |

FUNGICIDE ACTIVITY

The compounds of the present invention have been found to control fungi, particularly plant pathogens. When employed in the treatment of plant fungal diseases, the compounds are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 4 lb/A. The compounds of the invention may also be used to protect stored grain and other non-plant loci from fungal infestation.

Representative fungal disease organisms controlled include:
Alternaria brassicicola (leaf spot of brassicas),
Alternaria mali (leaf spot of apples),
Alternaria tenuis (leaf spot),
Botrytis cinerea (grey mold),
Cochliobolus sativus (spot blotch),
Colletotrichum coffeanum (coffee berry disease),
Colletotrichum lindemuthianum (anthracnose of bean),
Erysiphe graminis hordeii (barley powdery mildew),
Erysiphe graminis tritici (wheat powdery mildew),
Fusarium culmorum (head blight),
Fusarium oxysporum fsp phaseolicola,
Gerlachia nivalis (snow mold),
Leptosphaeria nodorum (glume blotch),
Phytophthora citricola,
Phytophthora parasitica (black shank),
Plasmopara viticola (grape downy mildew),
Podosphaera leucotricha (apple powdery mildew),
Pseudocercosporella herpotrichoides (cereal eyespot),
Puccinia recondita (brown rust),
Pyrenophora teres (net blotch),
Pyricularia oryzae (rice blast),
Pythium ultimum (damping off),
Rhizoctonia cerealis (sharp eyespot of wheat),
Rhizoctonia solani (sheath blight),
Rhyncosporium secalis (leaf scald),
Septoria tritici,
Sclerotium rolfsii (white rot),
Sclerotinia sclerotiorum,
Uncinula necator (grape powdery mildew),
Ustilago maydis (bunt of wheat),
Verticillium albo-atrum (wilt of tomatoes), and
Venturia inaequalis (apple scab).

The following experiments were used to evaluate the efficacy against a variety of different organisms that cause plant diseases of the compounds identified in Table I.

The test compounds were formulated for application by dissolving 50 mg of the compound into 1.25 ml of solvent. The solvent was prepared by mixing 50 ml of "Tween 20" (polyoxyethylene (20) sorbitan monolaurate emulsifier) with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Table II | Host |
|---|---|---|
| Erysiphe graminis tritici (powdery mildew) | ERYSGT | wheat |
| Pyricularia oryzae (rice blast) | PYRIOR | rice |
| Puccinia recondita | PUCCRT | wheat |

-continued ment. The effectiveness of test compounds in controlling disease was rated using the following scale.

TABLE II

| Compound | FUNGICIDE DATA | | | | |
|---|---|---|---|---|---|
| | ERYSGT | PYRIOR | PUCCRT | LETPNO | PLASVI |
| 1 | +++ | ++ | +++ | +++ | +++ |
| 2 | +++ | +++ | +++ | + | ++ |
| 3 | + | + | + | + | +++ |
| 4 | + | − | − | − | + |
| 5 | +++ | +++ | +++ | − | ++ |
| 6 | +++ | ++ | +++ | +++ | +++ |
| 7 | − | − | − | − | − |
| 8 | +++ | + | + | + | +++ |
| 9 | − | − | − | − | ++ |
| 10 | +++ | +++ | +++ | ++ | +++ |
| 11 | +++ | ++ | +++ | ++ | +++ |
| 12 | +++ | +++ | +++ | + | +++ |
| 13 | +++ | + | +++ | ++ | +++ |
| 14 | +++ | +++ | +++ | + | +++ |
| 15 | | | | | |
| 16 | ++ | ++ | +++ | + | +++ |
| 17 | +++ | +++ | ++ | + | +++ |
| 18 | | | | | |
| 19 | | | | | |
| 20 | +++ | +++ | +++ | + | +++ |
| 21 | + | + | ++ | + | ++ |
| 22 | | | | | |
| 23 | + | + | +++ | + | +++ |
| 24 | − | + | + | + | +++ |
| 25 | + | + | ++ | − | +++ |
| 26 | − | + | ++ | − | ++ |
| 27 | +++ | +++ | +++ | − | +++ |
| 28 | +++ | + | +++ | +++ | +++ |
| 29 | +++ | ++ | +++ | + | +++ |
| 30 | +++ | +++ | +++ | − | +++ |
| 31 | + | + | +++ | + | ++ |
| 32 | +++ | ++ | +++ | ++ | +++ |
| 33 | +++ | + | ++ | − | ++ |
| 34 | − | + | + | − | − |
| 35 | − | − | +++ | − | − |
| 36 | +++ | +++ | ++ | + | +++ |
| 37 | +++ | + | ++ | ++ | +++ |
| 38 | | | | | |
| 39 | | | | | |
| 40 | ++ | + | ++ | + | +++ |
| 41 | +++ | ++ | +++ | + | +++ |
| 42 | − | − | + | − | + |
| 43 | − | − | − | − | − |
| 44 | +++ | + | +++ | + | + |
| 45 | +++ | +++ | +++ | − | +++ |
| 46 | + | − | + | + | − |
| 47 | ++ | + | | − | + |
| 48 | + | − | | − | + |
| 49 | + | − | + | − | +++ |
| 50 | | | | | |
| 51 | +++ | ++ | − | +++ | ++ |

0 = not tested against specific organism
− = 0–19% control at 400 ppm
+ = 20–89% control at 400 ppm
++ = 90–100% control at 400 ppm
+++ = 90–100% control at 100 ppm

| Pathogen | Designation in Table II | Host |
|---|---|---|
| tritici (leaf rust) | | |
| Leptosphaeria nodorum (glume blotch) | LEPTNO | wheat |
| Plasmopara viticola (downy mildew) | PLASVI | grape |

The formulated technical compounds were sprayed on all foliar surfaces of the host plants to past run-off. Single pots of each host plant were placed on raised, revolving pedestals in a fume hood. Test solutions were sprayed on all foliar surfaces. All treatments were allowed to dry and the plants were inoculated with the appropriate pathogens within 24 hours.

Table II reports the activity of typical compounds of the present invention when evaluated in this experi-

INSECTICIDE ACTIVITY

The compounds of formula (I) show activity against a number of insects, mites, and nematodes. More specifically, the compounds show activity against cotton aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indian meal moth, leaf rollers, corn earworm, European corn borer, cabbage worm, cabbage looper, cotton bollworm, bagworm, eastern tent caterpillar, beet armyworm, tobacco budworm, sod webworm, and fall armyworm. The compounds also show activity against German cockroach, which is a member of the order Orthoptera. Other typical members of this order are Asian cockroach, oriental cockroach, American cockroach, lubber grasshopper, differential grasshopper, redlegged grasshopper, migratory grasshopper, American grasshopper, vagrant grasshopper, and house cricket. The compounds also show activity against corn rootworm, which is a member of the order Coleoptera. Other typical members of this order are western spotted cucumber beetle, Colorado potato beetle, confused flour beetle, Mexican bean beetle, plum curculio, Egyptian alfalfa weevil, alfalfa weevil, rice water weevil, southern corn billbug, boll weevil, and sweetpotato weevil.

The compounds of formula (I) are useful for reducing populations of insects, mites, and nematodes and are used in a method of inhibiting an insect, mite, or nematode population which comprises applying to a locus of the insect, mite, or nematode an effective insect-, mite-, or nematode-inactivating amount of a compound of formula (I). The "locus" of insects, mites, or nematodes is a term used herein to refer to the environment in which the insects, mites, or nematodes live or where their eggs are present, including the air surrounding them, the food they eat, the ground in which they live, or objects which they contact. For example, plant-ingesting insects or mites can be controlled by applying the active compound to plant parts, which the insects or mites eat, particularly the foliage. It is contemplated that the compounds might also be useful to protect textiles, paper, stored grain, or seeds by applying an active compound to such substance. The term "inhibiting an insect, mite, or nematode" refers to a decrease in the numbers of living insects, mites or nematodes; or a decrease in the number of viable insect, mite, or nematode eggs. The extent of reduction accomplished by a compound depends, of course, upon the application rate of the compound, the particular compound used, and the target insect, mite, or nematode species. At least an insect-inactivating, mite-inactivating or nematode inactivating amount should be used. The terms "insect-inactivating amount", "mite-inactivating amount" and "nematode-inactivating amount" are used to describe the amount, which is sufficient to cause a measurable reduction in the treated insect, mite, or nematode population. Generally an amount in the range from about 1 to about 1000 ppm active compound is used.

The compounds identified in Table I were tested for miticidal and insecticidal activity against eight species. Results are reported in Table III. The following abbreviations are used in the Table III:
ALH refers to aster leafhopper
BAW refers to beet armyworm
CA refers to cotton aphid
NEM refers to peanut rootknot nematode
SCRW refers to southern corn rootworm
TBW refers to tobacco budworm
TSSM refers to two spotted spider mite
GECR refers to German cockroach In conducting evaluations of insecticidal activity, each test compound was formulated as a 400 ppm solution, and this solution was then diluted with water to give lesser concentrations. The 400 ppm solution was prepared by combining 19.2 mL of 0.05% solution of Tween 20 (polyoxyethylene (20) sorbitan monolaurate) in water with a solution of 8 mg of the compound in 0.8 mL of acetone/EtOH (9/1).

Activity against aster leafhopper (*Macrosteles fascifrons*) was tested as follows. The test was run using concentrations of 400 ppm and 50 ppm. One ounce plastic cups containing a cotton wick was sprayed with 0.4 mL of formulated material using a flat-fan nozzle. The excess moisture was allowed to evaporate. Then five to ten carbon dioxide anesthetized adult leafhoppers were added to each cup. The cups were capped and held at room temperature for 24 hours. Percent mortality was then determined.

Activity against beet armyworm (*Spodoptera exiqua*) was evaluated as follows. The test is run using concentrations of 400 ppm and 50 ppm. A general purpose lepidoptera artificial diet was diluted to half strength with a 5% non nutritive agar. 8 mL of this diet material was dispensed into one ounce diet cups. One hour prior to treatment, 35 to 40 eggs were dispensed onto the diet surface. The cups were then sprayed with formulated material through a flat-fan nozzle. Treated cups were air dried prior to sealing with plastic caps. The cups were held for 6 days at room temperature. Activity was then rated based on the total number of live and dead larvae, and on the size of live larvae.

Activity against cotton aphid (*Aphis gossypii*) and two spotted spider mite (*Tetranychus urticae*) was evaluated as follows. Golden crookneck squash plants were grown to the expanded cotyledon stage (about 6 to 8 days). The plants were infested with cotton aphids and two spotted spider mites 16 to 24 hours before application of the test material by transfer of infested foliage cut from a stock colony. Immediately prior to spray application of the test material the transfer foliage is removed from the squash plants. The test is run using concentrations of 400 ppm and 50 ppm. The plants are sprayed with test solution using an atomizing sprayer at 17 psi. Both surfaces of the leaves are covered until runoff, and then allowed to dry. Activity of each compound was determined three days after treatment. Activity was rated as a percent based on the mites/aphids present in plants sprayed with solvent alone.

Activity against peanut rootknot nematode (*Meloidogyne arenaria*) was evaluated as follows. Five untreated cucumber seeds are placed into the bottom of a clear one ounce cup, 20 g of clean white sand is added, and the cups were sprayed while rotating on a pedestal allowing 1.0 mL of a 400 ppm solution to be deposited on the sand. To each cup was dispensed 2.5 to 3.0 mL of deionized water containing 300 to 500 nematodes. The cups were held for 10 to 12 days in an environmental growth chamber at a temperature of 76° to 85° F. and ambient humidity of 50 to 60%. After 10 to 12 days the cups were evaluated by inverting the cup and observing nematode mortality and feeding damage to the cucumber plants.

Activity on Southern corn rootworm (*Diabrotica undecimpuctata howardi* Barber) was evaluated by adding one mL of test solution containing a predetermined concentration of test compound to a cup containing a kernel of corn in 16 g of sterile soil. This produces a soil concentration of 24 ppm. After 1.5 to 2 hours of drying, five 4th instar corn rootworm larvae were added to the individual cups. Mortality was measured at 3–4 days by emptying the cup onto a pan and inspecting the soil for live rootworms.

Activity against tobacco budworm (*Heliothis virescens*) was evaluated as follows. A general purpose lepidoptera artificial diet was diluted to half strength with a 5% non nutritive agar. 8 mL of this diet material was dispensed into each one ounce diet cup. One hour prior to treatment 18 to 20 eggs were dispensed onto the diet surface. The cups were then sprayed with formulated material through a flat-fan nozzle. The test was run using concentrations of 400 ppm and 50 ppm. Treated cups were air dried prior to sealing with plastic caps. The cups were held for 6 days at room temperature. Activity was then rated based on the total number of live and dead larvae, and on the size of live larvae.

Activity against German cockroach (*Blattella germanicus*) was evaluated as follows. 8 mL of alfalfa based green insect diet material was dispensed into a one ounce diet cup. The cups were then sprayed with formulated material through a flat-fan nozzle. The test was run using concentrations of 400 ppm and 50 ppm. Treated cups were air dried for 24 hours and infested with five late third or early fourth instar German cockroaches. The cups were capped and held for ten days in an environmental growth chamber at a temperature of 76°–85° C. Activity was then rated based on the total number of live and dead insects.

TABLE III

| | INSECTICIDE, MITICIDE, AND NEMATICIDE DATA | | | | | | | |
|---|---|---|---|---|---|---|---|---|
| Compound | ALH 400 ppm 50 ppm | BAW 400 ppm 50 ppm | CA 400 ppm 50 ppm | NEM 400 ppm 50 ppm | SCRW 400 ppm 50 ppm | TBW 400 ppm 50 ppm | TSSM 400 ppm 50 ppm | GECR 400 ppm 50 ppm |
| 1 | 100 | 100 | 0 | 100 | 80 | 0 | 0 | 20 |
|   | 100 | 100 | 0 | — | — | 100 | 0 | 0 |
| 2 | | | | | | | | |
| 3 | | | | | | | | |
| 4 | | | | | | | | |
| 5 | 100 | 100 | 100 | 0 | 100 | 100 | 100 | 100 |
|   | — | — | — | — | — | — | — | — |
| 6 | 100 | 100 | 0 | 100 | 0 | 100 | 0 | 20 |
|   | 100 | 100 | 0 | — | — | 100 | 0 | 40 |
| 7 | 80 | 100 | 100 | 0 | 0 | 100 | 100 | 0 |
|   | 100 | 100 | 100 | — | — | 100 | 100 | 0 |
| 8 | | | | | | | | |
| 9 | | | | | | | | |
| 10 | | | | | | | | |
| 11 | | | | | | | | |
| 12 | 100 | 100 | 100 | 100 | 0 | 100 | 100 | 60 |
|   | 80 | 100 | 100 | 100 | — | 70 | 90 | 0 |
| 13 | 100 | 100 | 100 | | | 100 | 100 | |
|   | — | — | — | | | — | — | |
| 14 | | | | | | | | |
| 15 | | | | | | | | |
| 16 | 100 | 100 | 100 | 100 | 80 | 100 | 100 | 40 |
|   | 80 | 100 | 100 | — | — | 100 | 100 | 0 |
| 17 | | | | | | | | |
| 18 | | | | | | | | |
| 19 | | | | | | | | |
| 20 | 0 | 0 | 0 | 0 | 0 | 0 | 0 | 0 |
|   | — | — | — | — | — | — | — | — |
| 21 | 60 | 0 | 100 | 0 | 0 | 0 | 0 | 0 |
|   | — | — | — | — | — | — | — | — |
| 22 | | | | | | | | |
| 23 | 80 | 100 | 90 | 0 | 0 | 100 | 50 | 40 |
|   | 60 | 100 | 0 | — | — | 100 | 0 | 0 |
| 24 | | | | | | | | |
| 25 | 0 | 0 | 85 | 100 | 0 | 100 | 90 | 0 |
|   | — | — | — | — | — | — | — | — |
| 26 | 100 | 0 | 100 | 100 | 0 | 100 | 100 | — |
|   | — | — | — | — | — | — | — | |
| 27 | 100 | 100 | 100 | | 100 | 100 | 100 | |
|   | 100 | 100 | 90 | | 100 | — | — | |
| 28 | 100 | 100 | 100 | 100 | 0 | 100 | 100 | 80 |
|   | 100 | 100 | 100 | — | — | 100 | 100 | 0 |
| 29 | 100 | 100 | 100 | 100 | 100 | 100 | 100 | 20 |
|   | 100 | 100 | 90 | 0 | — | 100 | 100 | 0 |
| 30 | | | | | | | | |
| 31 | | | | | | | | |
| 32 | | | | | | | | |
| 33 | | | | | | | | |
| 34 | 20 | 100 | 0 | 40 | 0 | 80 | 0 | 0 |
|   | 40 | 0 | 0 | — | — | 0 | 0 | 0 |
| 35 | 80 | 100 | 0 | 0 | 0 | 80 | 0 | 0 |
|   | 0 | 100 | 0 | — | — | 0 | 0 | — |
| 36 | | | | | | | | |
| 37 | | | | | | | | |
| 38 | | | | | | | | |
| 39 | | | | | | | | |
| 40 | | | | | | | | |
| 41 | 100 | 100 | 100 | | | 100 | 100 | |
|   | — | — | — | | | — | — | |
| 42 | 60 | 0 | 0 | | | 0 | 0 | |
|   | — | — | — | | | — | — | |

TABLE III-continued

INSECTICIDE, MITICIDE, AND NEMATICIDE DATA

| Compound | ALH 400 ppm 50 ppm | BAW 400 ppm 50 ppm | CA 400 ppm 50 ppm | NEM 400 ppm 50 ppm | SCRW 400 ppm 50 ppm | TBW 400 ppm 50 ppm | TSSM 400 ppm 50 ppm | GECR 400 ppm 50 ppm |
|---|---|---|---|---|---|---|---|---|
| 43 | 0 | 0 | 0 | 0 | 0 | 0 | 0 | 0 |
|    | 0 | 0 | 0 | — | — | 0 | 0 | 0 |
| 44 | 0 | 100 | 100 | 0 | 100 | 100 | 50 | 20 |
|    | — | — | — | — | — | — | — | — |
| 45 | 40 | 100 | 100 | 100 | 0 | 100 | 60 | 20 |
|    | 60 | 100 | 100 | — | — | 100 | 40 | 0 |
| 46 | | | | | | | | |
| 47 | | | | | | | | |
| 48 | | | | | | | | |
| 49 | | | | | | | | |
| 50 | | | | | | | | |
| 51 | 100 | 100 | 0 | 0 | 100 | 100 | 0 | 0 |
|    | 100 | 100 | 0 | — | 0 | 100 | 0 | 0 |
| 52 | | | | | | | | |
| 53 | | | | | | | | |

COMPOSITIONS

The compounds of formula (I) are applied in the form of compositions which are important embodiments of the invention, and which comprise a compound of formula (I) and a phytologically-acceptable inert carrier. The compositions are either concentrated formulations which are dispersed in water for application, or are dust or granular formulations which are applied without further treatment. The composition are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional non-ionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 1% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredient in the carrier. The most widely used carrier is water.

The compounds of formula (I) can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

| A. Emulsifiable Concentrate | |
|---|---|
| Compound of Formula (I) | 9.38% |
| "TOXIMUL D" | 2.50% |
| (nonionic/anionic surfactant blend) | |
| "TOXIMUL H" | 2.50% |
| (nonionic/anionic surfactant blend) | |
| "EXXON 200" | 85.62% |
| (naphthalenic solvent) | |
| B. Emulsifiable Concentrate | |
| Compound of Formula (I) | 18.50% |
| "TOXIMUL D" | 2.50% |
| "TOXIMUL H" | 2.50% |
| "EXXON 200" | 76.50% |
| C. Emulsifiable Concentrate | |
| Compound of Formula (I) | 12.50% |
| N-methylpyrrolidone | 25.00% |
| "TOXIMUL D" | 2.50% |
| "TOXIMUL H" | 2.50% |
| "EXXON 200" | 57.50% |
| D. Aqueous Suspension | |
| Compound of Formula (I) | 12.00% |
| "PLURONIC P-103" | 1.50% |
| (block copolymer of propylene oxide and ethylene oxide, surfactant) | |
| "PROXEL GXL" | .05% |
| (biocide/preservative) | |
| "AF-100" | .20% |
| (silicon based antifoam agent) | |
| "REAX 88B" | 1.00% |
| (lignosulfonate dispersing agent) | |
| propylene glycol | 10.00% |
| veegum | .75% |
| xanthan | .25% |
| water | 74.25% |

| -continued | |
|---|---|
| E. Aqueous Suspension | |
| Compound of Formula (I) | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |
| F. Aqueous Suspension | |
| Compound of Formula (I) | 12.50% |
| "MAKON 10" | 1.50% |
| "ZEOSYL 200" (silica) | 1.00% |
| "AF-100" | 0.20% |
| "POLYFON H" | 0.20% |
| (lignosulfonate dispersing agent) | |
| 2% xanthan hydrate | 10.00% |
| water | 74.60% |
| G. Suspension Concentrate | |
| Compound of formula (I) | 10.20% |
| "TERGITOL TMN-6" | 3.40% |
| "ZEOSYL 200" | 0.90% |
| 2% "KELZAN" solution | 8.60% |
| "AF-100" | 0.20% |
| water | 76.70% |
| G. Wettable Powder | |
| Compound of Formula (I) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |
| H. Granules | |
| Compound of Formula (I) | 5.0% |
| propylene glycol | 5.0% |
| Exxon 200 | 5.0% |
| Florex 30/60 granular clay | 85.0% |

We claim:
1. A compound of the formula (I):

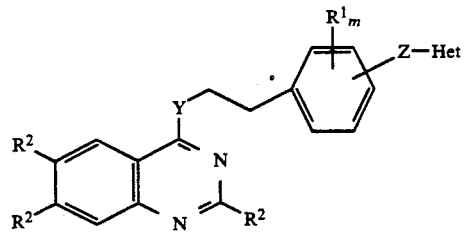

wherein:
Het is pyridyl, pyrazinyl, pyrimidinyl, or pyridizinyl, optionally substituted with one or more groups selected from halo, lower alkyl, lower alkoxy, haloalkyl, haloalkoxy, $NO_2$, CN, and lower alkoxy-carbonyl;
Z is a single bond connecting a carbon atom of Het to a carbon atom of the phenyl group, $CH_2$, NH, O, S, $-CH_2O-$, or $-OCH_2-$;
m is 4;
$R^1$ are independently H, halo, lower alkyl, lower alkoxy, haloalkyl, haloalkoxy, $NO_2$, CN, lower alkoxy-carbonyl, O-phenyl, or O-substituted phenyl;
substituted phenyl refers to phenyl substituted with lower alkyl, lower alkenyl, lower alkynyl, lower alkoxy, lower alkylthio, halo, hydroxy, $NO_2$, haloalkyl, haloalkoxy, haloalkylthio, CN, phenyl, O-phenyl, $C_1$-$C_4$ alkanoyloxy, or benzyloxy;

Y is CH$_2$, NR$^3$, or O, where R$^3$ is selected from H, lower alkyl, lower alkyl-carbonyl, lower alkyl-carbonyloxy, SOq-lower alkyl, SOq-phenyl or substituted phenyl; and q is an integer from 0 to 2;

R$^2$ are independently H, halo, lower alkyl, lower alkoxy, haloalkyl, haloalkoxy, NO$_2$, CN, or lower alkoxy-carbonyl;

or an N-oxide or salt thereof.

2. A compound of claim 1 wherein Het is pyridyl optionally substituted with one or more groups selected from halo, lower alkyl, lower alkoxy, haloalkyl, haloalkoxy, NO$_2$, CN, and lower alkoxy-carbonyl.

3. A compound of claim 2 wherein Het is 2-pyridyl optionally substituted with one or more groups selected from halo, lower alkyl, lower alkoxy, haloalkyl, haloalkoxy, NO$_2$, CN, and lower alkoxy-carbonyl.

4. A compound of claim 2 of formula (IA):

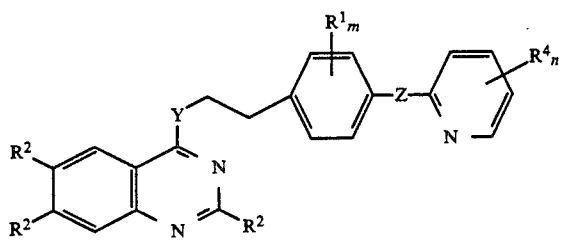

where n is 4; and R$^4$ are independently H, halo, lower alkyl, lower alkoxy, haloalkyl, haloalkoxy, NO$_2$, CN, and lower alkoxy-carbonyl.

5. A compound of claim 4 wherein n is 1 or 2 and R$^4$ is halo, loweralkyl, alkoxy, haloalkoxy, haloalkyl, cyano, or nitro.

6. A compound of claim 4 wherein 1, 2, or 3 of R$^4$ are halo and the remaining R$^4$ are H.

7. A pesticidal composition which comprises a compound of claim 1 in combination with an agronomically acceptable carrier.

8. A compound of formula (IB):

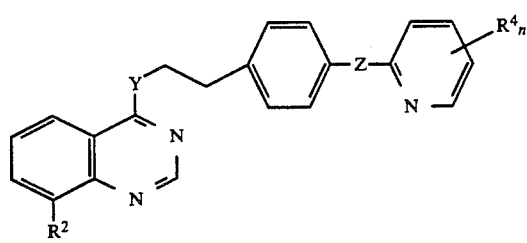

where n is 4; R$^4$ are independently H, halo, lower alkyl, lower alkoxy, haloalkyl, haloalkoxy, NO$_2$, CN, and lower alkoxy-carbonyl;

Z is a single bond connecting a carbon atom of Het to a carbon atom of the phenyl group, CH$_2$, NH, O, S, —CH$_2$O—, or —OCH$_2$—;

Y is CH$_2$, NR$^3$, or O, where R$^3$ is selected from H, lower alkyl, lower alkyl-carbonyl, lower alkyl-carbonyloxy, SOq-lower alkyl, SOq-phenyl or substituted phenyl; and q is an integer from 0 to 2;

substituted phenyl refers to phenyl substituted with lower alkyl, lower alkenyl, lower alkynyl, lower alkoxy, lower alkylthio, halo, hydroxy, NO$_2$, haloalkyl, haloalkoxy, haloalkylthio, CN, phenyl, O-phenyl, C$_1$-C$_4$ alkanoyloxy, or benzyloxy; and R$^2$ are independently H, halo, lower alkyl, lower alkoxy, haloalkyl, haloalkoxy, NO$_2$, CN, or lower alkoxy-carbonyl.

9. A compound of claim 8 wherein R$^2$ is fluoro.
10. A compound of claim 8 wherein R$^2$ is H.
11. A compound of claim 1 wherein Y is O.
12. A compound of claim 1 wherein Z is O.
13. A compound of claim 1 wherein Y and Z are both O.
14. A compound of claim 1 wherein Het is

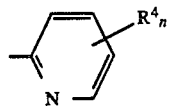

n is 1, and R$^4$ is haloalkyl.

15. A compound of claim 1 wherein Het is

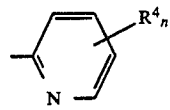

n is 1, 2, or 3, and R$^4$ are halo.

16. A compound of claim 8 which is 8-fluoro-4-(2-(4-(5-(trifluoromethyl)-2-pyridinyloxy)phenyl)ethoxy)-quinazoline.

17. A method of inhibiting an insect or mite population which comprises applying to the locus of the insect or mite an insect or mite inactivating amount of a compound of claim 1.

18. A method of inhibiting a nematode population which comprises applying to the locus of a nematode, a nematode inactivating amount of a compound of claim 1.

19. A plant fungicide method which comprises applying a plant pathogen inhibiting amount of a compound of claim 1 to the locus of a plant pathogen.

* * * * *